United States Patent [19]

Doyle et al.

[11] Patent Number: 4,670,464
[45] Date of Patent: Jun. 2, 1987

[54] INSECTICIDAL ESTER

[75] Inventors: Peter Doyle, Camberley; Alan J. Whittle, Aldershot, both of England

[73] Assignee: Imperial Chemical Industries PLC, London, England

[21] Appl. No.: 749,276

[22] Filed: Jun. 27, 1985

[30] Foreign Application Priority Data

Jul. 18, 1984 [GB] United Kingdom ............... 8418331

[51] Int. Cl.$^4$ ..................... A01N 53/00; C07C 121/75
[52] U.S. Cl. ..................................... 514/521; 558/407
[58] Field of Search ................. 260/465 D; 514/521; 558/407

[56] References Cited

U.S. PATENT DOCUMENTS

| | | | |
|---|---|---|---|
| 4,183,948 | 1/1980 | Huff | 514/521 |
| 4,252,820 | 2/1981 | Lantzsch | 514/521 |
| 4,510,098 | 4/1985 | Crosby | 558/407 |
| 4,510,160 | 4/1985 | Robson | 514/521 |
| 4,512,931 | 4/1985 | Robson | 558/407 |

FOREIGN PATENT DOCUMENTS 2044264A 10/1980 United Kingdom .
2064528A 6/1981 United Kingdom .
2075011A 11/1981 United Kingdom .
2074573A 11/1981 United Kingdom .

Primary Examiner—Dolph H. Torrence
Attorney, Agent, or Firm—Cushman, Darby & Cushman

[57] ABSTRACT

A process for the relative enrichment of a solution of α-cyano-4-fluoro-3-phenoxybenzyl 3-(Z-2-chloro-3,3,3-trifluoroprop-1-en-1-yl)-2,2-dimethylcyclopropane carboxylate with respect to the enantiomeric pair of isomers represented by (S)-α-cyano-4-fluoro-3-phenoxybenzyl (1R,cis)-3-(Z-2-chloro-3,3,3-trifluoroprop-1-en-1-yl)-2,2-dimethylcyclopropane carboxylate and (R)-α-cyano-4-fluoro-3-phenoxybenzyl (1S,cis)-3-(Z-2-chloro-3,3,3-trifluoroprop-1-en-1-yl)-2,2-dimethylcyclopropane carboxylate which comprises subjecting a solution comprising the enantiomeric pair of isomers (R)-α-cyano-4-fluoro-3-phenoxybenzyl (1R,cis)-3-(Z-2-chloro-3,3,3-trifluoroprop-1-en-1-yl)-2,2-dimethylcyclopropane carboxylate and (S)-α-cyano-4-fluoro-3-phenoxybenzyl (1S,cis)-3-(Z-2-chloro-3,3,3-trifluoroprop-1-en-1-yl)-2,2-dimethylcyclopropane carboxylate in an organic solvent to the action of a base to effect epimerization.

12 Claims, No Drawings

INSECTICIDAL ESTER

This invention relates to a novel insecticidally active product comprising a racemic mixture of two isomers.

The preparation of the compound (+)-α-cyano-4-fluoro-3-phenoxybenzyl (+)-cis/trans-3-(2-chloro-3,3,3-trifluoroprop-1-en-1-yl)-2,2-dimethylcyclopropane carboxylate is mentioned in European patent application publication No. 0008340. This compound is described as an unspecified mixture of cis and trans isomers, there being a possible eight cis-isomers and eight trans-isomers.

The present invention provides a novel insecticide product comprising just two isomers in the form of the racemate formed from (S)-α-cyano-4-fluoro-3-phenoxybenzyl (1R,cis)-3-(Z-2-chloro-3,3,3-trifluoroprop-1-en-1-yl)-2,2-dimethylcyclopropane carboxylate and its enantiomer, (R)-α-cyano-4-fluoro-3-phenoxybenzyl (1S,cis)-3-(Z-2-chloro-3,3,3-trifluoroprop-1-en-1-yl)-2,2-dimethylcyclopropane carboxylate, substantially free from other isomers of the same compound, and hereinafter called 'The Racemate'.

The Racemate may be obtained by chromatographic separation from mixtures of isomers, eg. from the product consisting of the four isomers obtained by esterifying (1RS,cis)-3-(Z-2-chloro-3,3,3-trifluoroprop-1-en-1-yl)-2,2-dimethylcyclopropane carboxylic acid with (RS)-4-fluoro-3-phenoxybenzaldehyde cyanhydrin. This product may be prepared most conveniently by reacting together 4-fluoro-3-phenoxybenzaldehyde with the acid chloride in the presence of an alkali metal cyanide, and water, optionally in the presence of a phase-transfer catalyst, eg. an onium salt, such as tetraalkylammonium halide, and an organic solvent. This product, consisting only of the four cis isomers with the Z-configuration in the 2-chloro-3,3,3-trifluoropropenyl group has not been described previously and also forms part of the present invention and is referred to hereinafter as 'The Starting Material'. It is itself a potent insecticide of greater relative efficacy than the previously described mixture of cis and trans isomers. However, The Racemate consisting of the two single isomers above mentioned is an even more effective insecticidal product.

By 'substantially free' as used herein is meant that the product containing the Racemate contains not more than 10% by weight of other isomers of the same compound.

The chromatographic separation of The Racemate may be accomplished using high performance liquid chromatographic means. A silica column is preferred, eluted with mixtures of an alkane, such as for example n-hexane, with a more polar material, such as an ester, for example ethyl acetate.

The Racemate may also be obtained in a crystalline form by a crystallisation technique.

This technique provides a process for obtaining a crystalline material (hereinafter called "the Product") consisting essentially of the enantiomeric pair of isomers represented by (S)-α-cyano-3-phenoxybenzyl (1R,cis)-3-(Z-2-chloro-3,3,3-trifluoroprop-1-en-1-yl)-2,2-dimethylcyclopropane carboxylate and (R)-α-cyano-3-phenoxybenzyl (1S,cis)-3-(Z-2-chloro-3,3,3-trifluoroprop-1-en-1-yl)-2,2-dimethylcyclopropane carboxylate in racemic proportions and substantially free from any other isomer of α-cyano-4-fluoro-3-phenoxybenzyl 3-(2-chloro-3,3,3-trifluoroprop-1-en-1-yl)-2,2-dimethylcyclopropane carboxylate, which comprises the steps of:

(a) forming a concentrated solution of The Starting Material with an organic solvent selected from lower alkanols containing up to 6 carbon atoms and liquid alkanes containing up to 8 carbon atoms, said solution containing from about 1:2 to about 1:4 parts by weight of the Starting Material:solvent, (b) adjusting the temperature of the solution to temperature within the range 17° C. to 20° C. and adding a quantity of crystals of the enantiomeric pair of isomers to the solution, the added crystals remaining thereafter in the solid undissolved state, (c) maintaining the solution at a temperature within the said range for a sufficient period to allow the crystalline material to precipitate from the solution, (d) separating the precipitated crystalline material from the solution, and (e) optionally, if required, subjecting the crystalline material to recrystallisation.

By 'substantially free' is meant that not more than 10% by weight of the Product is represented by the combined weight of any other isomers.

Preferred alkanol solvents are ethanol, iso-propanol, butan-1-ol, butan-2-ol, pentan-1-ol, and iso-propanol/t-butanol (1:1), isopropanol/1,2-ethanediol (2:1). Isopropanol is particularly prferred. Preferred liquid alkane solvents are n-hexane and n-heptane.

By a concentrated solution is meant preferably one containing from 1:2 to 1:4, and most preferably 1:3, parts by weight of The Starting Material:solvent.

The Starting Material used in this process may be contaminated with up to 10% by weight of the corresponding trans isomers and (E)-isomers. Preferably Starting Material of at least 95% purity is used since this usually provides the Product in higher yield and purity.

The process is performed using a quantity of added crystals of the enantiomeric pair of isomers. This appears to be an absolute requirement to effect precipitation of the Product from the solution. A quantity of the enantiomer pair of isomers of sufficient purity to be added may be obtained by subjecting the Starting Material to high performance liquid chromatography (HPLC) as described above to separate the desired enantiomeric pair of isomers from the other isomers present.

The process is preferably conducted by preparing the solution using slight warming if necessary, and then cooling the solution to a temperature in the range 17° to 20° C. for a period during which a substantial amount of Product crystallises. In a modified procedure the concentrated solution is added slowly to a mixture of the undissolved crystals and a little solvent, the rate of addition being adjusted to correspond with the rate of deposition of the Product. The period of addition may vary from a few hours to several days (eg. up to 10) according to the volume of solution to be added.

The temperature at which the Product crystallises out is critical. At temperatures below 17° C. the precipitate includes unwanted isomers; at temperatures above 20° C. no precipitation occurs at the concentrations used.

If recrystallisation is required to free the Product from other isomers which may have coprecipitated with the Product this may be achieved by using any suitable recrystallisation solvent, for example, the solvents referred to above as useful in the process for obtaining the Product.

The yield of Product may be substantially enhanced if at least step (c) of the above process is carried out in the presence of a base. This yield enhancement is the result of conversion by epimerisation of the enantiomeric pair of isomers represented by (R)α-cyano-4-fluoro-3-phenoxybenzyl (1R,cis)-3-(Z-2-chloro-3,3,3-trifluoroprop-1-en-1-yl)2,2-dimethylcyclopropane carboxylate and (S)-α-cyano-4-fluoro-3-phenoxybenzyl (1S,cis)-3-(Z-2-chloro-3,3,3-trifluoroprop-1-en-1-yl)-2,2-dimethylcyclopropane carboxylate to form in solution the enantiomeric pair of isomers represented by (S)-α-cyano-4-fluoro-3-phenoxybenzyl (1R,cis)-3-(Z-2-chloro-3,3,3-trifluoroprop-1-en-1-yl)-2,2-dimethylcyclopropane carboxylate and (R)-α-cyano-4-fluoro-3-phenoxybenzyl (1S,cis)-3-(z-2-chloro-3,3,3-trifluoroprop-2,2-dimethylcyclopropane carboxylate, which is thereafter precipitated from solution as the Product.

In its simplest form this aspect of the invention provides a process for the relative enrichment of a solution of α-cyano-4-fluoro-3-phenoxybenzyl-3-(Z-2-chloro-3,3,3-trifluoroprop-1-en-1-yl)-2,2-dimethylcyclopropane carboxylate with respect to the enantiomeric pair of isomers represented by (S)-α-cyano-4-fluoro-3-phenoxybenzyl (1R,cis)-3-(Z-2-chloro-3,3,3-trifluoroprop-1-en-1-yl)-2,2-dimethylcyclopropane carboxylate and (R)-α-cyano-4-fluoro-3-phenoxybenzyl (1S,cis)-3-(Z-2-chloro-3,3,3-trifluoroprop-1-en-1-yl)-2,2-dimethylcyclopropane carboxylate which comprises subjecting a solution comprising the enantiomeric pair of isomers (R)-α-cyano-4-fluoro-3-phenoxybenzyl (1R,cis)-3-(Z-2-chloro-3,3,3-trifluoroprop-1en-1yl)-2,2-dimethylcyclopropane carboxylate and (S)-α-cyano-4-fluoro-3-phenoxybenzyl (1S,cis)-3-(Z-2-chloro-3,3,3-trifluoroprop-1-en-1-yl)-2,2-dimethylcyclopropane carboxylate to the action of a base to effect epimerisation.

Alcohols such as those specified above are suitable solvents for this process. Isopropanol is particularly preferred. The base may be any organic or inorganic base which is stable under the reaction conditions. Organic amines, especially secondary and tertiary amines, and heterocyclic bases are useful, for example triethylamine, diisopropylamine, dibutylamine, and 2,2,6,6-tetramethylpiperidine. Diisopropylamine is particularly preferred as it provides a high degree of epimerisation whilst minimising the amount of decomposition of The Starting Material during the process. This decomposition appears to be mainly due to base-catalysed transesterification reactions involving the solvent alcohol. Another useful base is 1H,-1,5,9-triazabicyclo[4,4,0]dec-9-ene.

Also useful are inorganic bases such as alkali and alkaline earth metal hydroxides and carbonates, and alkali metal salts with weak organic acids such as acetic acid. Anhydrous potassium carbonate and potassium acetate are particularly preferred. Thus in one preferred embodiment of the process a solution of the Starting Material is passed through a column containing anhydrous potassium carbonate to effect the epimerisation.

The process is particularly useful to effect the enrichment of mother liquors from which the Product has been crystallised by the technique set out hereinabove. By the use of the combined enrichment and crystallisation processes all the Starting Material present may be effectively recovered in the form of the desired enantiomer pair.

In a further aspect therefore the invention provides an improved process for obtaining the Product which comprises the steps of:

(a) forming a concentrated solution of the Starting Material with an organic solvent selected from lower alkanols containing up to 6 carbon atoms and liquid alkanes containing from 5 to 8 carbon atoms, said solution containing from 1:2 to 1:4 parts by weight of the Starting Material:solvent, (b) adjusting the temperature of the solution to a temperature within the range 17° C. to 20° C. and adding a quantity of crystals of the enantiomeric pair of isomers to the solution, the added crystals remaining thereafter in the solid undissolved state, (c) maintaining the solution at a temperature within the said range for a sufficient period to allow the crystalline material to precipitate from the solution, (d) separating the precipitated crystalline material from the solution, and (e) optionally, if required, subjecting the crystalline material to recrystallisation, In a variation of this process the solution of Starting Material already containing the base may be added slowly to a stirred mixture of the seed crystals in a small amount of the solvent.

The Product is typically a white crystalline material with a melting point within the range of 60°–67° C. Product with a purity of at least 99% with respect to the Racemate has a melting point of 66.5°–67° C.

The Racemate may be used to combat and control infestations of insect pests and also other invertebrate pests, for example, acarine pests. The insect and acarine pests which may be combatted and controlled by the use of the Racemate include those pests associated with agriculture (which term includes the growing of crops for food and fibre products, horticulture and animal husbandry), forestry, the storage of products of vegetable origin, such as fruit, grain and timber, and also those pests associated with the transmission of diseases of man and animals.

In order to apply the Racemate to the locus of the pests they are usually formulated into compositions which include in addition to the insecticidally active ingredient suitable inert diluent or carrier materials, and/or surface active agents. The compositions may also comprise another pesticidal material, for example another insecticide or acaricide, or a fungicide, or may also comprise an insecticide synergist, such as for example dodecyl imidazole, safroxan, or piperonyl butoxide.

The compositions may be in the form of dusting powders wherein the Racemate is mixed with a solid diluent or carrier, for example kaolin, bentonite, kieselguhr, or talc, or they may be in the form of granules, wherein the Racemate is absorbed in a porous granular material for example pumice, gypsum or corn cob granules. Granules are particularly useful for combating soil borne insect pests, such as root worms of the genus Diabrotica, cutworms (Agrotis spp.) and wireworms (Agriotis spp.). Preferably, the granules contain from 1 to 2.5% by weight of the Racemate, which is absorbed onto the granule by, for example, spraying the granules with a solution of the Racemate in a volatile solvent which is subsequently evaporated from the surface of the granules. Such solutions may contain other ingredients, for example a resin to regulate the rate of release of the Racemate from the granules, or to help prevent premature disintegration of the granules. Granules may be applied to the soil either in a band between the furrows defining the crop rows, or broadcast, and may if desired be lightly incorporated in the soil, or they may be placed in the furrows themselves at the time of planting the crop. Application of granules at a rate from 5 to 25 lb/acre (approximately 5 to 25 kg/ha) is usually sufficient to control the pests, and a preferred rate is within the range 8 to 15 lb/acre (approximately 8 to 15 kg/ha) based on the Racemate.

Alternatively the compositions may be in the form of liquid preparations to be used as dips or sprays, which are generally aqueous dispersions or emulsions of the Racemate in the presence of one or more known wetting agents, dispersing agents or emulsifying agents (surface active agents).

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters of sulphuric acid, for example sodium lauryl sulphate, salts of sulphonated aromatic compounds, for example sodium dodecylbenzenesulphonate, sodium, calcium or ammonium lignosulphonate, or butylnaphthalene sulphonate, and a mixture of the sodium salts of diisopropyl- and triisopropylnaphthalene sulphonates. Suitable agents of the nonionic type include, for example, the condensation products of ethylene oxide or propylene oxide with fatty alcohols such as oleyl alcohol or cetyl alcohol, or with alkyl phenols such as octyl phenol, nonyl phenol and octyl cresol. Other non-ionic agents are the partial esters derived from long chain fatt acids and hexitol anhydrides, y the condensation products of the said partial esters with ethylene oxide, propylene oxide and the lecithins.

The compositions may be prepared by dissolving the Racemate in a suitable solvent, for example, a ketonic solvent such as diacetone alcohol, or an aromatic solvent such as trimethylbenzene and adding the mixture so obtained to water which may contain one or more known wetting, dispersing or emulsifying agents. Other suitable organic solvents are dimethyl formamide, ethylene dichloride, isopropyl alcohol, propylene glycol and other glycols, diacetone alcohol, toluene, kerosene, white oil, methylnaphthalene, xylenes and trichloroethylene, N-methyl-2-pyrrolidone and tetrahydrofurfuryl alcohol (THFA).

The compositions to be used as sprays may also be in the form of aerosols wherein the formulation is held in a container under pressure in the presence of a propellant such as fluorotrichloromethane or dichlorodifluoromethane.

The compositions which are to be used in the form of aqueous dispersions or emulsions are generally supplied in the form of a concentrate containing a high proportion of the Racemate the said concentrate to be diluted with water before use. These concentrates are often required to withstand storage for prolonged periods and after such storage, to be capable of dilution with water to form aqueous preparations which remain homogenous for a sufficient time to enable them to be applied by conventional spray equipment. The concentrates may contain 1-85% by weight of the Racemate. When diluted to form aqueous preparations such preparations may contain varying amounts of the active ingredient depending upon the purpose for which they are to be used. For agricultural or horticultural purposes, an aqueous preparation containing between 0.0001% and 0.1% by weight of the Racemate is particularly useful.

In use the compositions are applied to the pests, to the locus of the pests, to the habitat of the pests, or to growing plants liable to infestation by the pests, by any of the known means of applying pesticidal compositions, for example, by dusting or spraying.

The compositions of the invention are very toxic to wide varieties of insect and other invertebrate pests, including, for example, the following:
*Aphis fabae* (aphids)
*Megoura viceae* (aphids)
*Aedes aegypti* (mosquitoes)
*Dysdercus fasciatus* (capsids)
*Musca domestica* (houseflies)
*Pieris brassicae* (white bufferfly, larvae)
*Plutella maculipennis* (diamond back moth, larvae)
*Phaedon cochleariae (mustard beetle)*
*Tetranychus cinnabarinus* (carmine spider mite)
Aonidiella spp. (scale insects)
Trialeuroids spp. (white flies)
*Blattella germanica* (cockroaches)
*Spodoptera littoralis* (cotton leaf worm)
*Chortiocetes terminifera* (locusts)
Diabrotica spp. (rootworms)
Agrotis spp. (cutworms)

The compounds of the invention and compositions comprising them have shown themselves to be particularly useful in controlling lepidopteran pests of cotton, for example Spodoptera spp. and Heliothis spp. The properties of the compounds enable them to be used to combat pests which inhabit the soil, for example Diabrotica spp. They may also be used optionally in conjunction with other insecticides to combat public health pests such as flies. They are also very useful in combating insect and acarine pests which infest domestic animals, such as *Lucilia sericata,* and ixodid ticks such as Boophilus spp., Ixodes spp., Amblyomma spp., Rhipicephalus spp., and Dermaceutor spp. They are effective in combatting both susceptible and resistant strains of these pests in their adult, larval and intermediate stages of growth, and may be applied to the infested host animal by topical, oral or parenteral administration.

The invention is illustrated by the following Examples.

EXAMPLE 1

This Example illustrates the preparation of (RS)-α-cyano-4-fluoro-3-phenoxybenzyl (1RS,cis)-3-(Z-2-chloro-3,3,3-trifluoroprop-1-en-1-yl)-2,2-dimethylcyclopropane carboxylate.

A mixture of (1RS,cis)-1-chlorocarbonyl-3-(Z-2-chloro-3,3,3-trifluoroprop-1-en--yl)-2,2-dimethyl cyclopropane (0.52 g), 4-fluoro-3-phenoxybenzaldehyde (0.43 g), sodium cyanide (98 mg), n-hexane (5.0 cm$^3$), water (2.0 cm$^3$) and tetramethylammonium iodide (10 mg) was stirred for 16 hours at the ambient temperature (ca. 25° C.). After diluting with ethyl acetate the mixture was washed with saturated sodium bicarbonate solution, and with brine twice, the organic phase separated, dried over anhydrous magnesium sulphate, filtered and the filtrate concentrated by evaporation of the solvents under reduced pressure. The residual oil was purified by preparation column chromatography (silica column eluted successively with n-hexane containing 5% by volume and 10% by volume ethyl acetate. The fractions containing the product were identified by gas-chromatographic analysis (column temperature 225° C.). The fractions were bulked and the solvents removed by evaporation under reduced pressure to yield the product as an uncrystallisable oil in the form of a mixture of the four possible cis isomers with the Z-conformation in the chlorotrifluoropropenyl group, containing 29% by weight of each of (S)-α-cyano-4-fluoro-3-phenoxybenzyl (1S,cis)-3-(Z-2-chloro-3,3,3-trifluoroprop-1-en-1-yl)-2,2-dimethylcyclopropane carboxylate and its enantiomer, (R)-α-cyano-4-fluoro-3-phenoxybenzyl (1R,cis)-3-(Z-2-chloro-3,3,3-trifluoroprop-1-en-1-yl)-2,2-dimethylcyclopropane carboxylate, and 18% by weight of each of (S)-α-cyano-4-fluoro-3-phenoxybenzyl (1R,cis)-3-(Z-2-chloro-3,3,3-trifluoroprop-1-en-1-yl)-2,2-dimethylcyclopropane carboxylate and its enantiomer, (R)-α-cyano-4-fluoro-3-phenoxybenzyl (1S,cis)-3-(Z-2-chloro-3,3,3-trifluoroprop-1-en-1-yl)-2,2-dimethylcyclopropane carboxylate, the remaining 6% being impurities and residual solvent.

$^1$H nmr (CDCl$_3$)δ: 1.19–1.32 (complex, 6H); 2.00 (d, J=9 Hz, 1H); 2.28 (bdd, J=9,9 1H); 6.22 , 6.33 (s, 1H), 6.72-7.50 (m, 10H).

$^{19}$F nmr (CDCl$_3$)δ: −127.75 (td, J=7.28, 6.28, 1F); −69.32 (s, 3F).

Infra red (liquid paraffin): 1740, 1650, 1592, 1510, 1490, 1465, 1370, 1295, 1270, 1120, 750 cm$^{-1}$.

EXAMPLE 2

This Example illustrates the separation of the two racemic pairs of isomers present in the product of Example 1.

(i) A small amount of the product of Example 1 was subjected to high performance liquid chromatographic separation using a 5 cm silica analytical column eluted with n-hexane containing 4% by volume ethyl acetate at a rate of 1 cm$^3$/minute. Two peaks were observed at retention times of 6.39 and 7.66 minutes with relative areas of 4:1, corresponding to the isomer pair (S)-α-cyano-4-fluoro-3-phenoxybenzyl (1S,cis)-3-(Z-2-chloro-3,3,3-trifluoroprop-1-en-1-yl)-2,2-dimethylcyclopropane carboxylate and its enantiomer, (R)-α-cyano-4-fluoro-3-phenoxybenzyl (1R,cis)-3-(Z-2-chloro-3,3,3-trifluoroprop-1-en-1-yl)-2,2-dimethylcyclopropane carboxylate (hereinafter "Racemate A") and the isomer pair (S)-α-cyano-4-fluoro-3-phenoxybenzyl (1R,cis)-3-(Z-2-chloro-3,3,3-trifluoroprop-1-en-1-yl)-2,2-dimethylcyclopropane carboxylate and its enantiomer, (R)-α-cyano-4-fluoro-3-phenoxybenzyl (1R,cis)-3-(Z-2-chloro-3,3,3-trifluoroprop-1-en-1-yl)-2,2-dimethylcyclopropane carboxylate (hereinafter "Racemate B") respectively.

(ii) Using a semi-preparative h.p.l.c. apparatus and the conditions referred to in the previous paragraph, successive aliquots of the product of Example 1 (2.5 mg each) were separated. A total of 50 mg Racemate A (containing 6% by weight of Racemate B) and 15 mg Racemate B (containing 7% by weight of Racemate A) was obtained.

(iii) A preparative h.p.l.c. apparatus (Gilson) was employed to separate 500 mg of the product of Example 1 using the same conditions as in (i) above. There was obtained pure Racemate A (218 mg) and a mixture of Racemate A (20% by weight) and Racemate B (80% by weight) (63 mg).

The two racemic pairs of isomers can be distinguished by their proton n.m.r. spectra, the principal differences being as follows:

Nmr (CDCl$_3$)δ: Racemate A; 1.32 (s, 6H); 6.18 (s, 1H). Racemate B; 1.19 (s, 3H); 1.32 (s, 3H); 6.33 (s, 1H).

EXAMPLE 3

This Example illustrates the preparation of (RS)-α-cyano-4-fluoro-3-phenoxybenzyl (1RS,cis)-3-(Z-2-chloro-3,3,3-trifluoroprop-1-en-1-yl)-2,2-dimethylcyclopropane carboxylate.

Thionyl chloride (90 cm$^3$) containing dimethylformamide (0.5 cm$^{-1}$) was added to a stirred mixture of (1RS,cis)-3-(Z-2-chloro-3,3,3-trifluoroprop-1-en-1-yl)-2,2-dimethylcyclopropane carboxylic acid (90.94 g) and toluene (225 cm$^3$) at the ambient temperature and the resultant mixture stirred for a further 16 hours after which the volatile portion was removed by evaporation under reduced pressure. The residual oil was shown by infra red spectroscopy to consist principally of (1RS,cis)-1-chlorocarbonyl-3-(Z-2-chloro-3,3,3-trifluoroprop-1-en-1-yl)-2,2-dimethylcyclopropane. This was mixed with 4-fluoro-3-phenoxybenzaldehyde (76.92 g) and the mixture was added to a stirred mixture of sodium cyanide (22.0 g), water (71 cm$^3$) containing 1% by weight of a wetting agent 'Synperonic' NX, (registered Trade Mark), and toluene (32 cm$^3$) maintained at 35° C., over a period of 1 hour. Stirring was continued for 4 hours after which the reaction mixture was cooled to the ambient temperature, and extracted with diethyl ether (300 cm$^3$). The ethereal extract was washed with saturated sodium bicarbonate solution (100 cm$^3$) and with brine (2×100 cm$^3$) and concentrated by evaporation under reduced pressure to yield (RS)-α-cyano-4-fluoro-3-phenoxybenzyl (1RS,cis)-3-(Z-2-chloro-3,3,3-trifluoroprop-1-en-1-yl)-2,2-dimethylcyclopropane carboxylate as a colourless oil (147 g). Analysis by gas-chromatography indicated that the product was 93% pure and consisted on the four cis isomers in the proportions indicated in Example 1.

EXAMPLE 4

This Example illustrates the process for obtaining the Product by crystallisation and enriching the mother liquors with respect to the Racemate.

A solution of (RS)-α-cyano-4-fluoro-3-phenoxybenzyl (1RS-cis)-3-(Z-2-chloro-3,3,3-trifluoroprop-1-en-1-yl)-2,2-dimethylcyclopropane carboxylate (47.0 g, prepared by the method of Example 2) in dry isopropanol (141 cm$^3$) containing diisopropylamine (3.5 cm$^3$) was added dropwise over a period of 7 days to a stirred mixture of a crystalline solid material consisting of (R)-α-cyano-4-fluoro-3-phenoxybenzyl (1S,cis)-3-(Z-2-chloro-3,3,3-trifluoroprop-1-en-1-yl)-2,2-dimethylcyclopropane and (S)-α-cyano-4-fluoro-3-phenoxybenzyl (1R,cis)-3-(Z-2-chloro-3-3,3,3-trifluoroprop-1-en-1-yl)-2,2-dimethylcyclopropane in fluoroprop-1-en-1-yl)-2,2-dimethylcyclopropane in racemic proportions (1.0 g) and dry isopropanol (5.0 cm$^3$) whilst the temperature was maintained at 17.5° C. When the addition was complete the mixture was stirred for a further 24 hours and the solid precipitate collected by filtration, washed on the filter with dry isopropanol (5.0 cm$^3$, cooled to 0° C.) and dried to give a crystalline Product (mp 66.5°–67.0° C.) consisting of (R)-α-cyano-4-fluoro-3-phenoxybenzyl (1S,cis)-3-(Z-2-chloro-3,3,3-trifluoroprop-1-en-1-yl)-2,2-dimethylcyclopropane carboxylate and (S)-α-cyano-4-fluoro-3-phenoxybenzyl (1R,cis)-3-(Z-2-chloro-3,3,3-trifluoroprop-1-en-1-yl)-2,2-dimethylcyclopropane carboxylate in racemic proportions (19.0 g 99% pure by nmr analysis).

¹H nmr (CDCl₃)δ: 1.19 (s, 3H); 1.32 (s, 3H); 2.0 (d, J=9 Hz, 1H); 2.28 (dd, J=9,9 Hz, 1H); 6.33 (s, 1H); 6.72–7.50 (m, 10H).

¹⁹F nmr (CDCl₃)δ: (84.26 MHz) −127.75 (td J=7.28, 6.28, 1F); −69.32 (s, 3F).

Infra red (KBr): 1745, 1652, 1592, 1513, 1495, 1421, 1305, 1300, 1275, 1197, 1137, 1129, 1082, 820, 805, 752 cm⁻¹.

The mother liquors were concentrated by evaporation of solvent under reduced pressure and the residue dissolved in ethyl acetate, the solution washed with water and brine and dried over anhydrous magnesium sulphate and concentrated by evaporation of the solvent under reduced pressure to yield a mixture of the four cis isomers in a ratio of approximately 1:1:1:1, thus indicating an overall enhancement of the mother liquors with respect to the Racemate during this course of the process.

EXAMPLE 5

This Example illustrates the improved activity of the invention products in comparison with known insecticides. The LC₅₀ value of the products was determined in tests against larval *Heliothis virescens* (tobacco budworms—an important pest of cotton) by placing the larvae on leaves which had been treated by spraying with compositions containing various concentrations (rates) of the products expressed in parts per million. The mortality was observed at the different rates and the LC₅₀ value (concentration required to kill 50% of the pests present) determined by calculation. The results are set out in the following Table both in form of the LC₅₀ value and also the ratio of activity with respect to cyhalothrin (a known insecticide), where a numerical value greater than one indicates a higher level of activity.

| Product | LC₅₀ ppm | Ratio v. cyhalothrin |
|---|---|---|
| Cyhalothrin (known product)* | 3.4 | 1.0 |
| Cyfluthrin (known product)⁺ | 4.8 | 0.71 |
| Product of Example 1 | 0.9 | 3.78 |
| Racemate B | 0.44 | 7.73 |

*Cyhalothrin is (±)-α-cyano-3-phenoxybenzyl (±)-cis-(Z-2-chloro-3,3,3-trifluoroprop-1-en-1-yl)-2,2-dimethylcyclopropane carboxylate.
⁺Cyfluthrin is (±)-α-cyano-4-fluoro-3-phenoxybenzyl (±)-cis/trans-3-(2,2-dichlorovinyl)-2,2-dimethylcyclopropane carboxylate.

We claim:

1. A process for the relative enrichment of a solution of α-cyano-4-fluoro-3-phenoxybenzyl 3-(Z-2-chloro-3,3,3-trifluoroprop-1-en-1-yl)-2,2-dimethylcyclopropane carboxylate with respect to the enantiomeric pair of isomers represented by (S)-α-cyano-4-fluoro-3-phenoxybenzyl (1R,cis)-3-(Z-2-chloro-3,3,3-trifluoroprop-1-en-1-yl)-2,2-dimethylcyclopropane carboxylate and (R)-α-cyano-4-fluoro-3-phenoxybenzyl (1R,cis)-3-(Z-2-chloro-3,3,3-trifluoroprop-1-en-1-yl)-2,2-dimethylcyclopropane carboxylate which comprises subjecting a solution comprising the enantiomeric pair of isomers (R)-α-cyano-4-fluoro-3-phenoxybenzyl (1R,cis)-3-(Z-2-chloro-3,3,3-trifluoroprop-1-en-1-yl)-2,2-dimethylcyclopropane carboxylate and (S)-α-cyano-4-fluoro-3-phenoxybenzyl (1S,cis)-3-(Z-2-chloro-3,3,3-trifluoroprop-1-en-1-yl)-2,2-dimethylcyclopropane carboxylate in an organic solvent to the action of a base to effect epimerisation.

2. A process according to claim 1 wherein the organic solvent is a lower alkanol containing up to six carbon atoms.

3. A process according to claim 2 wherein the lower alkanol is isopropanol.

4. A process according to claim 1 wherein the base is secondary or tertiary amine or a heterocyclic base.

5. A process according to claim 4 wherein the base is diisopropylamine, 2,2,6,6-tetramethylpiperidine or 1H-1,5,9-triazabicyclo[4,4,0]-dec-9-ene.

6. A process for obtaining an enhanced yield of a crystalline material consisting essentially of the enantiomeric pair of isomers represented by (S)-α-cyano-4-fluoro-3-phenoxybenzyl (1R,cis)-3-(Z-2-chloro-3,3,3-trifluoroprop-1-en--yl)-2,2-dimethylcyclopropane carboxylate and (R)-α-cyano-4-fluoro-3-phenoxybenzyl (1S,cis)-3-(Z-2-chloro-3,3,3-trifluoroprop-1-en-1-yl)-2,2-dimethylcyclopropane carboxylate in racemic proportions and substantially free from any other isomer of α-cyano-4-fluoro-3-phenoxybenzyl-3-(2-chloro-3,3,3-trifluoroprop-1-en-1-yl)-2,2-dimethylcyclopropane carboxylate, which comprises the steps of:

(a) Forming a concentrated solution of (RS)-α-cyano-3-phenoxybenzyl (1RS,cis)-3-(Z-2-chloro-3,3,3-trifluoroprop-1-en-1-yl)-2,2-dimethylcyclopropane carboxylate with an organic solvent selected from lower alkanols containing up to six carbon atoms, (b) adjusting the temperature of the solution to a temperature within the range 17° C. to 20° C. and adding a quantity of crystals of the enantiomeric pair of isomers to the solution, the added crystals remaining thereafter in the solid undissolved state, (c) maintaining the solution at a temperature within the said range for a sufficient period to allow the crystalline material to precipitate from the solution, (d) separating the precipitated crystalline material from the solution, and (e) optionally, if required, subjecting the crystalline material to recrystallisation, characterised in that a base is present during at least step (c) of the process whereby at least a proportion of the enantiomeric pair of isomers represented by (R)-α-cyano-4-fluoro-3-phenoxybenzyl (1R,cis)-3-(ZR,cis)-3-(Z-2-chloro-3,3,3-trifluoroprop-1-en-1-yl)-2,2-dimethylcyclopropane carboxylate (S)-α-cyano-4-fluoro-3-phenoxybenzyl (1R,cis)-3-(Z-2-chloro-3,3,3-trifluoroprop-1-en-1-yl)-2,2-dimethylcyclopropane carboxylate is converted to the enantiomeric pair of isomers represented by (S)-α-cyano-4-fluoro-3-phenoxybenzyl (1R,cis)-3-(Z-2-chloro-3,3,3-trifluoroprop-1-en-1-yl)-2,2,-dimethylcyclopropane carboxylate and (R)-α-cyano-4-fluoro-3-phenoxybenzyl (1S,cis)-3-(Z-2-chloro-3,3,3-trifluoroprop-1-en-1-yl)-2,2-dimethylcyclopropane carboxylate.

7. The process substantially according to claim 6 with the modification that the solutions also contains the base and is added slowly to a mixture of the undissolved crystals of the enantiomeric pair of isomers and the organic solvent whilst maintaining the temperature within the range 17° to 20° C.

8. The enantiomeric pair of isomers consisting of (R)-α-cyano-4-fluoro-3-phenoxybenzyl (1S,cis)-3-(Z-2-chloro-3,3,3-trifluoroprop-1-en-1-yl)-2,2-dimethylcyclopropane carboxylate and (S)-α-cyano-4-fluoro-3-phenoxybenzyl (1R,cis)-3-(Z-2-chloro-3,3,3-trifluoroprop-1-en-1-yl)-2,2-dimethylcyclopropane carboxylate in racemic proportions and substantially free of any other isomer of α-cyano-4-fluoro-3-phenoxybenzyl-3-(2-chloro-3,3,3-trifluoroprop-1-en-1-yl)-2,2-dimethylcyclopropane carboxylate.

9. The enantiomeric pair of isomers according to claim 8 in crystalline solid form having a melting point within the range 60°–67° C.

10. An insecticidal composition comprising an insecticidally effective amount of the enantiomeric pair of isomers according to claim 8 and substantially free of any other isomer of α-cyano-4-fluoro-3-phenoxybenzyl 3-(2-chloro-3,3,3-trifluoroprop-1-en-1-yl)-2,2-dimethylcyclopropane carboxylate, in association with an agriculturally and horticulturally acceptable insecticidally inert diluent or carrier.

11. A method of controlling insect pests at a locus which comprises applying to the locus an insecticidally effective amount of a composition according to claim 10.

12. (RS)-α-cyano-4-fluoro-3-phenoxybenzyl (1RS,cis)-3-(Z-2-chloro-3,3,3-trifluoroprop-1-en-1-yl)-2,2-dimethylcyclopropane carboxylate, substantially free from admixture with any trans isomer, or any (E)-isomer.

* * * * *